(12) United States Patent
Imperiali et al.

(10) Patent No.: US 7,964,729 B2
(45) Date of Patent: Jun. 21, 2011

(54) SOX-BASED KINASE SENSOR

(75) Inventors: Barbara Imperiali, Cambridge, MA (US); Elvedin Lukovic, Cambridge, MA (US); Dora Carrico-Moniz, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 905 days.

(21) Appl. No.: 11/511,050

(22) Filed: Aug. 28, 2006

(65) Prior Publication Data

US 2008/0050761 A1    Feb. 28, 2008

(51) Int. Cl.
*C07D 215/00* (2006.01)
*C07D 215/12* (2006.01)
*C07D 215/14* (2006.01)
*C07D 215/16* (2006.01)
*C07D 215/36* (2006.01)
*C07D 215/38* (2006.01)
*A61K 38/00* (2006.01)

(52) U.S. Cl. ........ 546/152; 546/171; 546/172; 546/174; 546/176; 546/177; 546/179; 514/7.5

(58) Field of Classification Search ............... 546/152, 546/171, 172, 174, 176, 177, 179; 514/7.5
See application file for complete search history.

(56) References Cited

U.S. PATENT DOCUMENTS

| 5,118,499 | A * | 6/1992 | Theodoropulos .......... 424/78.23 |
| 6,310,211 | B1 | 10/2001 | Vaillancourt et al. |
| 6,906,194 | B2 | 6/2005 | Imperiali et al. |
| 7,262,282 | B2 | 8/2007 | Imperiali et al. |
| 7,589,209 | B2 * | 9/2009 | Canary et al. .................. 546/159 |
| 2005/0080243 | A1 | 4/2005 | Imperiali et al. |
| 2005/0227365 | A1 * | 10/2005 | Canary et al. .................... 436/81 |
| 2007/0196860 | A1 | 8/2007 | Gee et al. |
| 2008/0009026 | A1 | 1/2008 | Gee |
| 2008/0085529 | A1 | 4/2008 | Imperiali et al. |

FOREIGN PATENT DOCUMENTS

| JP | 11335354 | * 12/1999 |
| JP | 2006213615 | * 10/2005 |
| WO | WO 2004/007461 | * 1/2004 |
| WO | WO 2005037859 | 4/2005 |
| WO | WO 2008/016762 A1 | 2/2008 |

OTHER PUBLICATIONS

Blake et al., Dalton Transactions, 2004, (17), 2771-2779.*
Ning et al., Journal of Organic Chemistry, 1999, 64(24) 8855-8861.*
Okamoto et al., Tetrahedron Letters, 1988, 29(9), 971-4, Abstract.*
Hill et al., WO 2001/44274, Jun. 21, 2001.*
Walkup et al., Journal of Organic Chemistry, 1998, 63(19), 6727-6731.*
Jotterand et al., Journal of Organic Chemistry, 2001, 66(9), 3224-3228.*
JP 2006213615 translated abstract.*

(Continued)

*Primary Examiner* — Taylor Victor Oh
(74) *Attorney, Agent, or Firm* — Wolf, Greenfield & Sacks, P.C.

(57) ABSTRACT

Peptidyl sensors comprise a metal-binding peptide and one or two kinase recognition sequences with a hydroxyamino acid that can be phosphorylated in the presence of a kinase.

10 Claims, 4 Drawing Sheets

OTHER PUBLICATIONS

Newton, A.C., "Protein Kinase C: Structural and Spatial Regulation by Phosphorylation, Cofactors, and Macromolecular Interaction," *Chem. Rev.*, 2001, 2353-2364.

Nishikawa, K., et al., "Determination of the Specific Substrate Sequence Motifs of Protein Kinase C Isozymes," *J. Biol. Chem.*, 1997, 272, 952-960.

Sainlos, M., et al., "Tools for investigating peptide-protein interactions: peptide incorporation of environment-sensitive fluorophores via on-resin derivatization," *Nature Protocols*, 2007, vol. 2, No. 12, p. 3201-2309.

Sainlos, M., et al., "Synthesis of Anhydride Precursors of the Environment-Sensitive Fluorophores 4-DMAP and 6-DMN," *Nature Protocols*, 2007, vol. 2, No. 12, p. 3219-3225.

Sainlos, M., et al., "Tools for Investigating Peptide-Protein Interactions: Peptide Incorporation of Environment-Sensitive Fluorphores," *Nature Protocols*, 2007, vol. 2, No. 12 p. 3210-3218.

Shults, M.D., et al. "Versatile Fluorescence Proves of Protein Kinase Activity," *J. Am. Chem. Soc.*, 2003, 125, p. 14248-14249.

Vazquez, M.E., et al., "Photophysics and Biological Applications of the Environment-Sensitive Fluorophore 6-$N$,$N$-Dimethylamino-2,3-Naphthalimide," *J. Am. Chem. Soc.*, 2005, 127, p. 1300-1306.

Venkatraman, P., et al., "Fluorogenic Probes for Monitoring Peptide Binding to Class II MHC Proteins in Living Cells," *Nature Chemical Biology*, Apr. 2003, 3, No. 4, p. 222-228.

Office Action for U.S. Appl. No. 10/681,427 dated Sep. 15, 2004.

Office Action for U.S. Appl. No. 10/819,587 dated Oct. 18, 2006.

International Search Report for Application No. PCT/US2004/032733 dated Apr. 28, 2005.

Written Opinion for Application No. PCT/US2004/032733 dated Oct. 27, 2005.

Carrigan, C.N. et al., "The Engineering of Membrane-Permeable Peptides," *Analytical Biochemistry*, 341, pp. 290-298, 2005.

Chen, C.-A. et al., "Biosensors of Protein Kinase Action: From In Vitro Assays to Living Cells," *Biochimica et Biophysica Acta*, 1697, pp. 39-51, 2004.

Chen, C.-A. et al., "Design and Synthesis of a Fluorescent Reporter of Protein Kinase Activity," *J. Am. Chem. Soc.*, 124, pp. 3840-3841, 2002.

Higashi, H. et al., "Imaging of cAMP-Dependent Protein Kinase Activity in Living Neural Cells Using a Novel Fluorescent Substrate," *FEBS Letters*, 414, pp. 55-60, 1997.

Hofmann, R.M. et al., "Fluorescent Monitoring of Kinase Activity in Real Time: Development of a Robust Fluorescence-Based Assay for Abl Tyrosine Kinase Activity," *Bioorganic & Medicinal Chemistry Letters*, 11, pp. 3091-3094, 2001.

Kurokawa, K. et al., "A Pair of Fluorescent Resonance Energy Transfer-Based Probes for Tyrosine Phosphorylation of the CrkII Adaptor Protein in Vivo," *The Journal of Biological Chemistry*, 276, No. 33, pp. 31305-31310, 2001.

Lawrence, D., "Chemical Probes of Signal-Transducing Proteins," *Acc. Chem. Res.*, 36, pp. 401-409, 2003.

Lindgren, M. et al. "Cell-Penetrating Peptides," *Trends Pharmacol. Sci.*, 21, pp. 99-103.

McIlroy, B. K. et al., "A Continuous Fluorescence Assay for Protein Kinase C," *Analytical Biochemistry*, 195, pp. 148-152, 1991.

Nagai, Y. et al., "A Fluorescent Indicator for Visualizing cAMP-Induced Phosphorylation in Vivo," *Nature Biotech*, 18, pp. 313-316, 2000.

Ohuchi, Y. et al., "A Fluorescent-Labeled Oligopeptide for Monitoring PKA-Mediated Phosphorylation," *Analyst*, 125(11) pp. 1905-1907, Nov. 2000.

Post, P. et al., "A Genetically Engineered, Protein-Based Optical Biosensor of Myosin II Regulatory Light Chain Phosphorylation," *The Journal of Biological Chemistry*, 269 No. 17, pp. 12880-12887, 1994.

Rothman, D.M. et al., "Chemical Approaches for Investigating Phosphorylation in Signal Transduction Networks," *Trends in Cell Biology*, 15, No. 9, pp. 502-510, 2005.

Sato, M. et al., "Fluorescent Indicators for Imaging Protein Phosphorylation in Single Living Cells," *Nature Biotechnology*, 20, pp. 287-294, 2002.

Shults M.D. et al., "Modular and Tunable Chemosensor Scaffold for Divalent Zinc.," *J. Am. Chem. Soc.*, 125, pp. 10591-10597, 2003.

Shults M.D. et al., "A Multiplexed Homogeneous Fluorescence-Based Assay for Protein Kinase Activity in Cell Lysates," *Nature Methods*, pp. 1-7, 2005.

Shults, M.D. et al., "Optimal Sox-BASED Fluorescent Chemosensor Design for Serine/Threonine Protein Kinases," *Analytical Biochemistry*, 352, pp. 198-207, 2006.

Shults, M.D. et al., "Versatile Fluorescence Probes of Protein Kinase Activity," *J. Am. Chem. Soc.*, 125, pp. 14284-14249, 2003.

Ting, A. Y. et al., "Genetically Encoded Fluorescent Reporters of Protein Tyrosine Kinase Activities in Living Cells," *PNAS*, 98, No. 26, pp. 15003-15008, 2001.

Violin, J.D. et al., "A Genetically Encoded Fluorescent Reporter Reveals Oscillatory Phosphorylation by Protein Kinase C," *The Journal of Cell Biology*, 161, No. 5, pp. 899-909, 2003.

Wadia, J.S., et al., "Protein Transduction Technology," *Curr. Opin. Biotechnol.*, 13(1), pp. 52-56, Feb. 2002.

Wang, Q. et al., "Self-Reporting Fluorescent Substrates of Protein Tyrosine Kinases," *J. Am. Chem. Soc.*, 128, pp. 1808-1809, 2006.

Wright, D. E. et al., "Fluorometric Assay for Adenosine 3', 5'—Cyclic Monophosphate-Dependent Protein Kinase and Phosphoprotein Phosphatase Activities," *Proceedings of the National Academy of Sciences of the United States of America*, 78, No. 10, pp. 6048-6050, 1981.

Yeh, R. et al., "Real Time Visualization of Protein Kinase Activity in Living Cells," *The Journal of Biological Chemistry*, 277 No. 13, pp. 11527-11532, 2002.

Zhang, J. et al., "Genetically Encoded Reporters of Protein Kinase A Activity Reveal Impact of Substrate Tethering," *PNAS*, 98, No. 26, pp. 14997-15002, 2001.

International Preliminary Report On Patentability in corresponding PCT Application No. PCT/US2004/032733, date Apr. 20, 2005, 10 pgs.

A list of peptides that can be phosphorylated (and the corresponding kinases) found at online at www.neb.com/neb/tech/tech_resource/protein_tools/substraye_recognition.html (this website as it existed on Sep. 26, 2003 is provided).

Royzen, et al., "A Sensitive Probe for the Detection of Zn(II) by Time-Resolved Fluorescence," JACS, 2006, pp. 3854-3855, No. 128.

International Search Report and Written Opinion for International Patent Application No. PCT/US07/76959 dated Oct. 7, 2008.

* cited by examiner

A.

B.

C.

D.

SOX-BASED KINASE SENSOR

GOVERNMENT FUNDING

This invention was made with U.S. government support under grant numbers GM064346 and 5-T32-CA09112-30 awarded by the National Institutes of Health. The U.S. government has certain rights in this invention.

FIELD OF THE INVENTION

The present invention relates to Sox-based kinase sensor.

BACKGROUND OF THE INVENTION

The present invention provides sensors to monitor protein kinase activity continuously with a fluorescent readout. The sensor requires minimal perturbation of a protein kinase peptide substrate. The fluorescence response with respect to time over the course of the reaction corresponds to enzyme activity. The sensor of the present invention can be used in high-throughput screening of inhibitors or substrates, detection of activity in cell extracts or enzyme purifications, spatial or temporal localization of kinase activity in a cell, and elucidation of complicated signal transduction pathways.

Protein kinases are involved in all aspects of regulation within cells. A protein kinase catalyzes the transfer of a phosphoryl group from adenosine triphosphate (ATP) to a serine, threonine or tyrosine residue in a peptide or protein sequence. Each kinase is specific for the amino acids surrounding the residue to be phosphorylated. The traditional method for assaying kinase activity is discontinuous and requires $^{32}$P-labelled ATP, which requires special handling. Many companies market specialized fluorescent kinase assay systems, all of which are discontinuous, requiring sampling of the reaction mixture followed by additional handling steps to label the product of the reaction with a fluorescent moiety (e.g., Promega, Panvera, Calbiochem, Cell Signaling Technology, Molecular Devices, DiscoveRx, Upstate, PerkinElmer). A continuous fluorescent assay that can be performed in real time is of great utility. Currently, few examples of sensors capable of such assays exist. Approaches include: environment-sensitive fluorophores near the phosphorylation site (Wright, D. E. et al. *Proc. Natl. Acad. Sci. USA* 1981, 78, 6048-6050; McIlroy, B. K. et al. *Anal. Biochem.* 1991, 195, 148-152; Higashi, H. et al. *FEBS Lett.* 1997, 414, 55-60; Post, P. L. et al. *J. Biol. Chem.* 1994, 269, 12880-12887), FRET pairs flanking a sequence which undergoes a conformational change upon phosphorylation (Nagai, Y. et al. *Nat. Biotech.* 2000, 18, 313-316; Ohuchi, Y. et al. *Analyst* 2000, 125, 1905-1907; Zhang, J. et al. *Proc. Natl. Acad. Sci. USA* 2001, 98, 14997-15002; Ting, A. Y. et al. *Proc. Nat. Acad. Sci. USA* 2001, 98, 15003-15008; Hofmann, R. M. et al. *Bioorg. Med. Chem. Lett.* 2001, 11, 3091-3094; Kurokawa, K. at el. *J. Biol. Chem.* 2001, 276, 31305-31310; Sato, M. et al. *Nat. Biotech.* 2002, 20, 287-294; Violin, J. D. et al. *J. Cell Biol.* 2003, 161, 899-909), or $Ca^{2+}$ chelation between the phosphate and internal chelator causing disruption of PET-quenching (Chen, C.-A.; et al. *J. Am. Chem. Soc.* 2002, 124, 3840-3841). A majority of these sensors have very modest fluorescence increases or sometimes decreases, with the notable exception of 1.5-2.5-fold increases in the probes reported by Lawrence and coworkers (Chen 2002, supra; Yeh, R.-H.; et al. *J. Biol. Chem.* 2002, 277, 11527-11532; Wang, Q.; et al. *J. Am. Chem. Soc.* 2006, 128, 1808-1809). However, these types of probes, with fluorophores adjacent to the phosphorylated residue or very large fluorophores, may interfere with their recognition by and reactivity with certain kinases.

U.S. Patent Application Publication No. 2005/0080243 disclosed linear Sox peptide sensors that include a metal binding amino acid residue and a kinase recognition sequence with a hydroxyamino acid that can be phosphorylated in the presence of a kinase. The metal-binding amino acid residue is located on either side (N-terminally or C-terminally) of the hydroxyamino acid and is preferably separated from that recognition sequence by a peptide that is capable of assuming a β-turn conformation ("a β-turn sequence"). In some cases, the β-turn sequence is separated from the hydroxyamino acid by another amino acid.

BRIEF SUMMARY OF THE INVENTION

The present invention provides novel metal binding compounds of the formulae (I) to (XII) that exhibit chelation-enhanced fluorescence (CHEF) upon binding to $Mg^{2+}$.

The present invention further provides peptidyl sensors which include a metal-binding peptide of the present invention and at least one kinase recognition sequence with a hydroxyamino acid that can be phosphorylated in the presence of a kinase. The peptide sensors detect sulfation of a hydroxyamino acid as well.

DETAILED DESCRIPTION OF THE INVENTION

Figure 1:
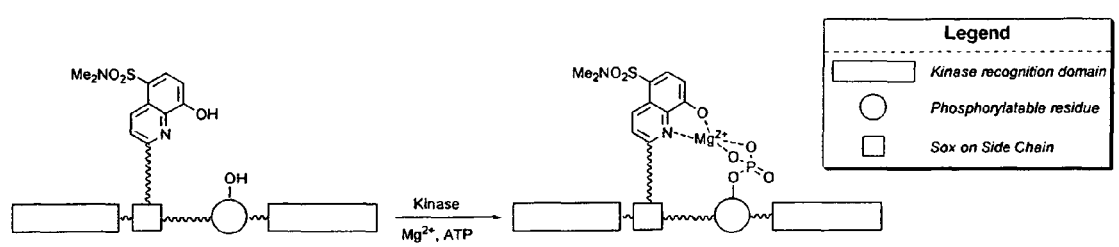
FIG. 1 is a schematic illustration of a Sox-based kinase sensor.

The present invention provides metal binding compounds that are useful in building sensors containing kinase-recognition motifs for detecting kinase activity. Sensors in accordance with the present invention are illustrated in FIG. 1. The sensors comprise a metal binding site, a phosphorylation site and at least one kinase recognition motif.

Definitions

The term "hydroxy" means the —OH group.

The term "amino" means the —NR'R" group, where R' and R" are each independently hydrogen or alkyl.

The term "thiol" means the —SR' group, where R' is hydrogen.

The term "halogen" means a chlorine, bromine, iodine, or fluorine atom.

The term "alkyl" means a hydrocarbon group that may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "aryl" means a polyunsaturated, aromatic hydrocarbon group having a single ring (monocyclic) or multiple rings (bicyclic or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "heteroaryl" means an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "heterocyclyl" or "heterocyclic", which are synonymous as used herein, means a saturated or unsaturated ring containing at least one heteroatom (typically 1 to 5 heteroatoms) selected from nitrogen, oxygen or sulfur. The heterocyclyl ring may be monocyclic or bicyclic. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "electron-withdrawing group" means a group which causes a dipole moment in the direction of the group. Suitable electron-withdrawing groups include but are not limited to halo (preferably chloro), haloalkyl (preferably trifluoromethyl), nitro, cyano, sulfonamido, sulfone, and sulfoxide.

The term "ring" means a compound whose atoms are arranged in formulas in a cyclic form. The ring compound can be either carbocyclic or heterocyclic.

The term "carbocyclic" means a ring composed exclusively of carbon atoms.

The term "substituent" means an atom or a group that replaces another atom or group in a molecule.

The term "N-terminal protecting group" refers to a group that prevents undesirable reaction of the amino functional group during subsequent transformations, and includes, but is not limited to, benzyl, substituted benzyl, benzyloxycarbonyl (Cbz), tert-butoxycarbonyl (Boc), 9-fluorenylmethoxycarbonyl (Fmoc), trityl, N-veratyloxycarbonyl (N-Voc), N-allyloxycarbonyl (N-Alloc) and N-pentenoyl (N-Pent).

The term "C-terminal protecting group" refers to a group that prevents undesirable reaction of the carboxyl functional group and includes, but is not limited to, $C_{1-12}$ alkyl (e.g., tert-butyl) and $C_{1-12}$ haloalkyl.

The term "chelation-enhanced fluorescence (CHEF)" means fluorescence enhancement of a compound as a result of metal ion binding (chelation) to that compound.

The term "capping group" means a chemical group connected to the N- or C-terminus of a peptide to prevent the peptide from degrading.

Compounds

The compounds of the present invention contain a metal binding moiety. The compounds are generally referred to as "Sox" compounds.

In one embodiment, the metal binding compound of the present invention has the formula (I):

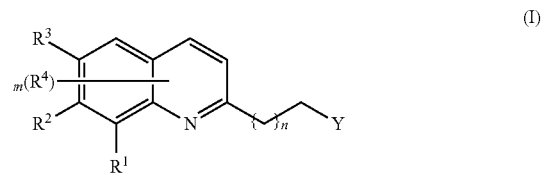

where $R^1$ is hydroxy, amino, or thiol;
$R^2$ and $R^3$ are each independently hydrogen, an electron-withdrawing group, or —$SO_2X$; or where $R^2$ and $R^3$ together with the carbon atoms, which they substitute form a 5- or 6-membered ring;
each $R^4$ is independently hydrogen, an electron-withdrawing group or —$SO_2X$, wherein $R^4$ can substitute any open valence of any ring within structure (I);
X is —OR' or —NR'R";
Y is halogen (preferably —Br or —Cl), —SH, —NR'R''', —CHO, or —$CO_2H$;
R' and R" are each independently hydrogen or $C_{1-6}$ alkyl;
R''' is hydrogen, $C_{1-6}$ alkyl or an N-protecting group;
n is 0, 1, 2, or 3; and
m is 1, 2, 3, 4, 5, 6 or 7,
wherein at least one of $R^2$, $R^3$ or $R^4$ is —$SO_2X$ and at least another one of $R^2$, $R^3$ or $R^4$ is an electron-withdrawing group.

In another embodiment, the metal-binding compound of the present invention has the formula (VIII):

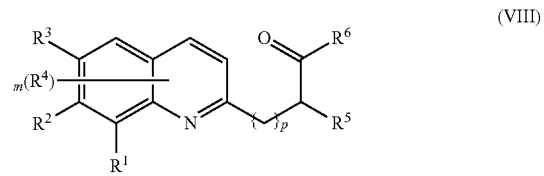

where $R^5$ is hydrogen or —NR'R''';
$R^6$ is —OH, —NR'R", or —H;
p is 1, 2 or 3;
$R^1$, $R^2$, $R^3$, $R^4$, R', R", R''' and m are as defined in formula (I).

In one preferred embodiment, the metal-binding compound is of the formula (IV):

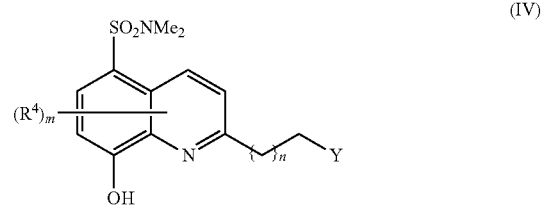

Where $R^4$, m, n and Y are as defined in formula (I).

In formula (I) and (VIII), $R^2$ and $R^3$ together with the carbons which they substitute can form a ring. When $R^2$ and $R^3$ form a ring, the metal binding compound can contain a 5- or 6-membered heterocyclic ring compound or a 5- or 6-membered carbocyclic ring compound. Preferably, $R^2$ and $R^3$ form a 5- or 6-N-containing heterocyclic ring.

In a preferred embodiment, the metal-binding compound can have the formula (V) or (X):

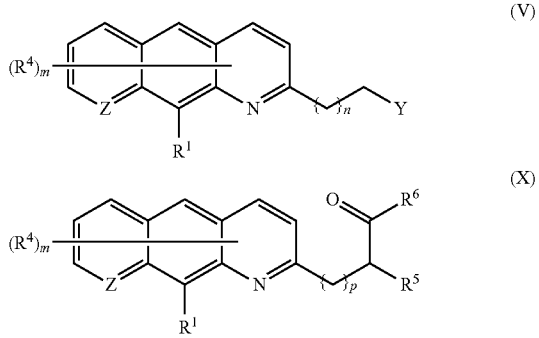

where Z is a —CH— or —N—; R¹, R⁴, X, R⁵, R⁶, R' R", R''', Y, m, n and p are as described above for formula (I) and (VIII), and
wherein at least one R⁴ is —SO₂X.

In formula (I), (IV) and (V), Y is preferably halogen.

In the various embodiments described above, R¹ is preferably —OH. X is preferably —NR'R''' (more preferably —NMe₂). m is preferably 1. n is preferably 0, 1 or 2 (more preferably 0 or 1). p is preferably 1, 2 or 3. At least one R⁴ is preferably present para to R¹. R⁴ is preferably —SO₂X.

In formula (VIII) and (X), R⁵ is preferably —NHR''' (more preferably NH-Fmoc). R⁶ is preferably —OH.

In the various embodiments described above, the electron-withdrawing group can be alkyl, halogen, —NR$^i$R$^{ii}$, —OR$^i$, —SR$^i$, —CN, —NO₂, =O, —OC(O)R$^i$, —C(O)R$^i$, —C(O)NR$^i$R$^{ii}$, —OC(O)NR$^i$R$^{ii}$, —NR$^{ii}$C(O)R$^i$, —NR$^i$C(O)NR$^{iii}$R$^{ii}$, —CO₂R$^i$, —NR$^i$R$^{ii}$, —NR$^{ii}$CO₂R$^i$, —SR$^i$, —S(O)R$^i$, —S(O)₂R$^i$, —S(O)₂NR$^i$R$^{ii}$, —NR$^i$S(O)₂R$^{ii}$, unsubstituted or substituted aryl, unsubstituted or substituted heteroaryl, and unsubstituted or substituted heterocyclyl, wherein R$^i$, R$^{ii}$ and R$^{iii}$ are each independently hydrogen or C$_{1-6}$ alkyl.

The metal-binding compounds of the present invention undergo chelation-enhanced fluorescence (CHEF) upon binding to Mg$^{2+}$. The fluorescence of the amino acid residues in accordance with the present invention increase by at least about 100%, preferably by at least about 400%, more preferably by at least about 800%, when bound to Mg$^{2+}$.

Peptides

The metal-binding compounds, such as formulae (VIII) and (X), can be formed into peptides using standard peptide synthesis (solid phase or solution phase). Standard peptide synthesis is well-known in the art. See, for example, *Fmoc Solid Phase Peptide Synthesis—A Practical Approach*, Oxford University Press, 2003, Eds W. C. Chan and P. D. White (ISBN 0 19 963 724 5); and *The Chemical Synthesis of Peptides*, Clarendon Press, Oxford, 1994, Jones, J. (ISBN 0 19 855839 2).

When the SOX compounds are coupled to peptide after synthesis, the peptide is first synthesized and protecting groups on the side chains of the peptide are selectively removed. Then the metal binding SOX compounds, such as formulae (I), can be coupled to the side chains of formed peptides using standard coupling methods. For example, when Y is halogen, the compound can be coupled to a residue containing a thiol group in its side chain (such as Cys), forming a thioether linkage. Alternatively, when Y is an amine, it can be coupled to a residue containing a carboxylic acid in its side chain (such as Asp or Glu), forming an amide linkage. Alternatively, when Y is thiol, it can be coupled to a residue containing a thiol group in its side chain (such as Cys), forming a disulfide linkage. Alternatively, when Y is a carboxylic acid, it can be coupled to a residue containing an amine in its side chain. The SOX-containing peptide is then deprotected and purified. Alternatively, when Y is an aldehyde, it can be coupled to a residue containing amine via reductive amination. Alternatively, a building block containing the SOX residue can be synthesized (i.e., see example section) and incorporated using standard peptide synthesis steps.

Selective deprotection of amino acids is well known in the art. A preferred method is to use orthogonal side-chain protection such as allyl (OAll) (for the carboxyl group in the side chain of glutamic acid or aspartic acid, for example), allyloxy carbonyl (Alloc) (for the amino nitrogen in the side chain of lysine or ornithine, for example), p-methoxytrityl (MMT) or acetamidomethyl (Acm) (for the sulfhydryl of cysteine). OAll and Alloc are easily removed by Pd, Acm is easily removed by iodine treatment, and MMT is easily removed by very mild acid treatment.

The metal binding compounds of the present invention are preferably within −5, −4, −3, −2, −1, 1, 2, 3, 4 or 5 residues from the kinase recognition sequence (Negative (−) positions indicate the compound is located on the N-terminal side of the kinase recognition sequence. Positive (+) positions indicate the compound is located on the C-terminal side of the kinase recognition sequence). In some cases the metal binding compounds may be located further from the kinase recognition sequence.

Phosphorylation sites in accordance with the present invention include hydroxyl-containing amino acids within kinase recognition motifs. Examples include naturally occurring hydroxyl-containing amino acid residues, such as serine, threonine and tyrosine, and non-naturally occurring hydroxyl-containing amino acid residues.

Any kinase recognition motif known in the art can be used in accordance with the present invention. Recognition sequences with acidic residues may show a lesser magnitude of fluorescence increase upon phosphorylation than comparable sequences, as the affinity of the unphosphorylated peptide for Mg$^{2+}$ increases under basic conditions. Examples of recognition motifs that can be monitored for phosphorylation using the metal binding peptides of the present invention are shown in Table I:

TABLE I

Examples of kinase recognition sequences

| Kinase | recognition motif |
|---|---|
| Protein kinase C (PKC) | -<u>Ser/Thr</u>-Phe-Arg-Arg-Arg- |
| cyclic-AMP dependent kinase (PKA) | -Leu-Arg-Arg-Ala-<u>Ser/Thr</u>-Leu- |
| Abelson kinase (Abl) | -Ile-<u>Tyr</u>-Ala-Ala-Pro-Phe- |

*The underlined residues are the phosporylation sites.

A list of other peptides that can be phosphorylated (and the corresponding kinases) is found in Table I of Pinna & Donella-Deana, Biochimica et Biophysica Acta 1222: 415-431 (1994); incorporated herein by reference in its entirety. Another list can be found at online at www.neb.com/neb/tech/tech_resource/protein_tools/substraye_recognition.html (a copy of this website as it existed on Sep. 26, 2003 is provided in an information disclosure statement submitted concurrently with this application; and is incorporated by reference in its entirety).

The peptide sensors according to the present invention have at least one kinase recognition sequence. In some cases, the residues on one side of the side chain to be phosphorylated are more important, however, it is clear that more residues might confer additional specificity. This specificity could play an important role in any assays that assess kinases in complex media, in particular in live cells or cell lysates where all cellular enzymes have the potential to interact with the substrate peptide. Added recognition elements can target the sensor more specifically to the desired kinase in competitive assays where several different kinases or isozymes of one kinase are present.

Assays

Fluorescence of the peptides is measured in the presence and absence of the $Mg^{2+}$. The reporter functionality is the unnatural Sox chromophore that undergoes chelation-enhanced fluorescence (CHEF) upon metal binding. The $Mg^{2+}$ affinity of the chemosensors is low ($K_D$=100-300 mM) when the phosphate group is not present, while phosphorylation significantly increases $Mg^{2+}$ affinity ($K_D$=0.1-20 mM). Thus, at a selected $Mg^{2+}$ concentration, a large portion of phosphopeptide exists in the bound, fluorescent state. In the presence of saturated $MgCl_2$, the Sox peptides exhibit a maximum emission at 485 nm with a maximum excitation at 360 nm. In addition, these peptides maintain striking luminescence properties of the fluorophore. The extinction coefficient and quantum yield values for representative chemosensor-$Mg^{2+}$ complexes are determined following quantitative amino acid analysis.

To solve for enzyme kinetic parameters for this reaction, determination of the initial rate of product formation from the increase in fluorescence intensity is necessary. With this sensor, a correction for the decrease in fluorescence intensity due to the starting material being consumed is needed to determine the rate of product formation from the initial slope. The fluorescence intensity at any given point can be determined from the following equation:

$$I(t) = f_S S(t) + f_P P(t) \quad (1)$$

where $I(t)$ is the fluorescence intensity, $S(t)$ is the amount of substrate in μM, $P(t)$ is the amount of product in μM, $f_S$ is the fluorescence intensity per μM of substrate, and $f_P$ is fluorescence intensity per μM of product. The amount of substrate and product at any given point are related by:

$$S(t) + P(t) = S_0 \quad (2)$$

where $S_0$ is the initial amount of substrate. Substitution of (2) into (1) followed by rearrangement, yields:

$$P(t) = \frac{I(t) - f_S S_0}{f_P - f_S} \quad (3)$$

The initial velocity of the reaction is the change in the amount of product over time, so taking the derivative of (3) with respect to time gives:

$$v = \frac{dP(t)}{dt} = \frac{\frac{dI(t)}{dt}}{f_P - f_S} \quad (4)$$

The initial slope of the reaction, $dI(t)/dt$, was measured within the first 5% of substrate turnover. The constants $f_P$ and $f_S$ were calculated from the slope of a line of fluorescence intensity versus concentration of P and S, respectively. A linear fit of a Hanes plot ([S]/V vs. V) was used to find $K_m$ and $V_{max}$.

The sensors of the present invention can be used in a method for detecting kinase activity. The method of the present invention comprises providing a sensor comprising one or two kinase recognition motifs containing a phosphorylation site, and a metal binding peptide comprising an amino acid residue, the side chain of which is modified with a compound of formula (I); contacting the sensor with a sample comprising $Mg^{2+}$, a phosphate source (eg ATP), and a kinase; and analyzing for the presence of a phosphorylated peptide product.

The method of the present invention can be used in vitro or in vivo. For in vitro applications, the reaction is typically conducted in a buffer containing $Mg^{2+}$ and a phosphate source. Suitable buffers include HEPES and TRIS. A preferred $Mg^{2+}$ source is $MgCl_2$. A preferred phosphate source is ATP.

Serine/threonine and tyrosine kinases can be used in the present invention. Exemplary Ser/Thr kinases include cAMP dependent protein kinase, protein kinase C, Ca/calmodulin-dependent kinases, AMP activated kinase, s6 kinases, eIF-2 kinases, p34$^{cdc2}$ protein kinase, mitogen-activated protein kinases, casein kinase-2, casein kinase-1, glycogen synthase kinase-3, AURORA, Akt, Erk, Jnk, CDK2, and exemplary Tyr-specific protein kinases include Src Abl, insulin receptor kinase and EGFR.

For in vitro applications, the concentration of kinase can range from about 0.5 nM to about 1 μM, typically not more than about 500 nM, and preferably not more than about 250 nM. The concentrations of sensor can vary, but usually ranges between about 0.01 μM to 0.1 mM. Adenosine 5'-triphosphate (ATP) is the preferred source of phosphate, in stock solutions of about 10-100 mM. Because most kinases have $K_m$ values for ATP in the range of about 10-150 μM, saturating concentrations of ATP are used to arrive at values of $K_m$ and $V_{max}$ for the substrates. For in vivo applications, when the sensor is internalized into a cell, sufficient kinases, $Mg^{2+}$ and phosphate sources exist in the cytosol. For in vivo sensing, a cellular internalization sequence can be included in the sensor design. Suitable cellular internalization sequences include Penetratins, HIV-Tat domains and poly-arginine sequences (Lindgren, M. et al. *Trends Pharmacol. Sci.* 2000, 21, 99-103; Wadia, J. S. et al. *Curr Opin. Biotech.* 2002, 13, 52-56; Carrigan, C. N. *Analyt. Biochem.* 2005, 341, 290-298).

For applications in which the kinase is dependent on cofactors, a source of cofactor is also included in the sample. For example, for PKC, sources of $Ca^{2+}$, phospholipid and diacylglycerol are needed.

The sensors of the present invention can be used to measure a kinase reaction continuously, as the metal-binding amino acid residues do not experience photobleaching.

EXAMPLES

Synthesis of Compounds:

The metal-binding compounds can be prepared based on the Skraup quinoline synthesis, the modified Friedlander quinoline synthesis, or the cyclization of ortho-2,4-dinitrophenyloxime derivatives with NaH and DDQ.

Scheme 1.
Synthetic approaches towards the extended linear Sox quinoline system.

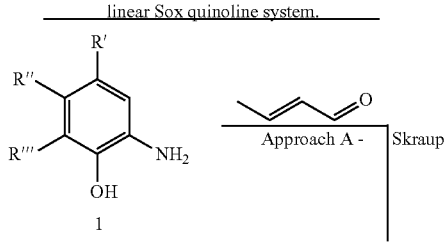

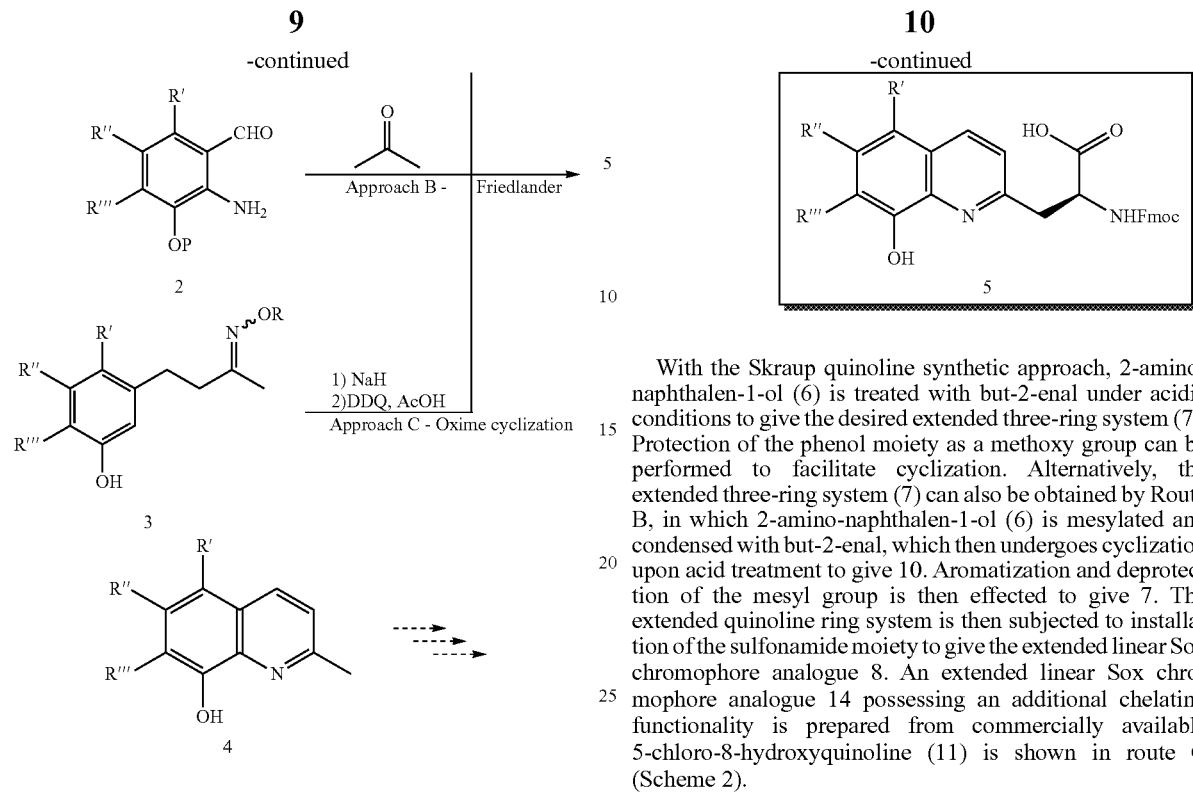

With the Skraup quinoline synthetic approach, 2-aminonaphthalen-1-ol (6) is treated with but-2-enal under acidic conditions to give the desired extended three-ring system (7). Protection of the phenol moiety as a methoxy group can be performed to facilitate cyclization. Alternatively, the extended three-ring system (7) can also be obtained by Route B, in which 2-amino-naphthalen-1-ol (6) is mesylated and condensed with but-2-enal, which then undergoes cyclization upon acid treatment to give 10. Aromatization and deprotection of the mesyl group is then effected to give 7. The extended quinoline ring system is then subjected to installation of the sulfonamide moiety to give the extended linear Sox chromophore analogue 8. An extended linear Sox chromophore analogue 14 possessing an additional chelating functionality is prepared from commercially available 5-chloro-8-hydroxyquinoline (11) is shown in route C (Scheme 2).

Scheme 2.
Skraup synthetic adaptation for the synthesis of the extended 8-hydroxyquinoline three-ring systems

ROUTE A

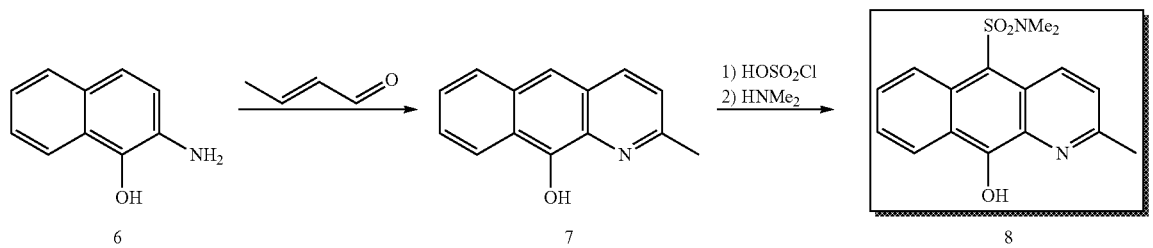

ROUTE B

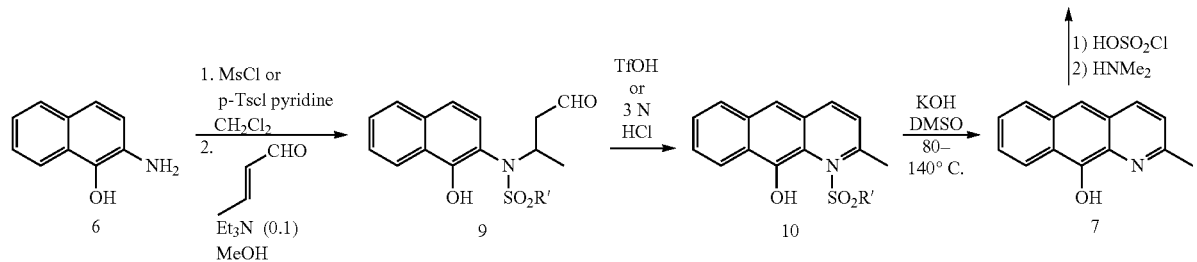

ROUTE C

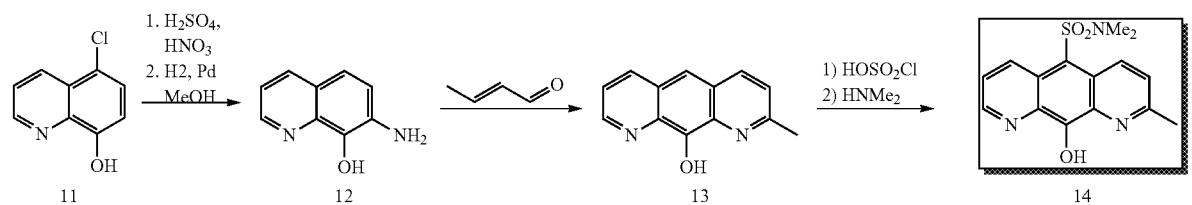

With the Friedlander quinoline synthesis approach, protection of the phenol group of commercially available 2-aminonaphthalen-1-ol (6) with methyl iodide is first effected to give the methoxy derivative 15. Protection of the aniline group with di-tert-butyldicarbonate is then followed to give the amide 16. Tert-butyloxycarbonyl directed lithiation of 16, alkylation with dimethylformamide and subsequent tert-butyloxycarbonyl deprotection with TFA result in the ortho-aminobenzaldehyde derivative 18. Once aldehyde 18 is obtained, cyclization with acetone is accomplished either by treatment with ZnCl$_2$ or with Bi(OTf)$_3$ to give the extended quinoline ring system 19. Deprotection of the methoxy group with BBr$_3$, followed by installation of the sulfonamide moiety as previously described, successfully affords the extended Sox quinoline analogue system 8.

Scheme 3.
Friedlander synthetic adaptation for the synthesis of the extended 8-hydroxyquinonline three-ring systems.

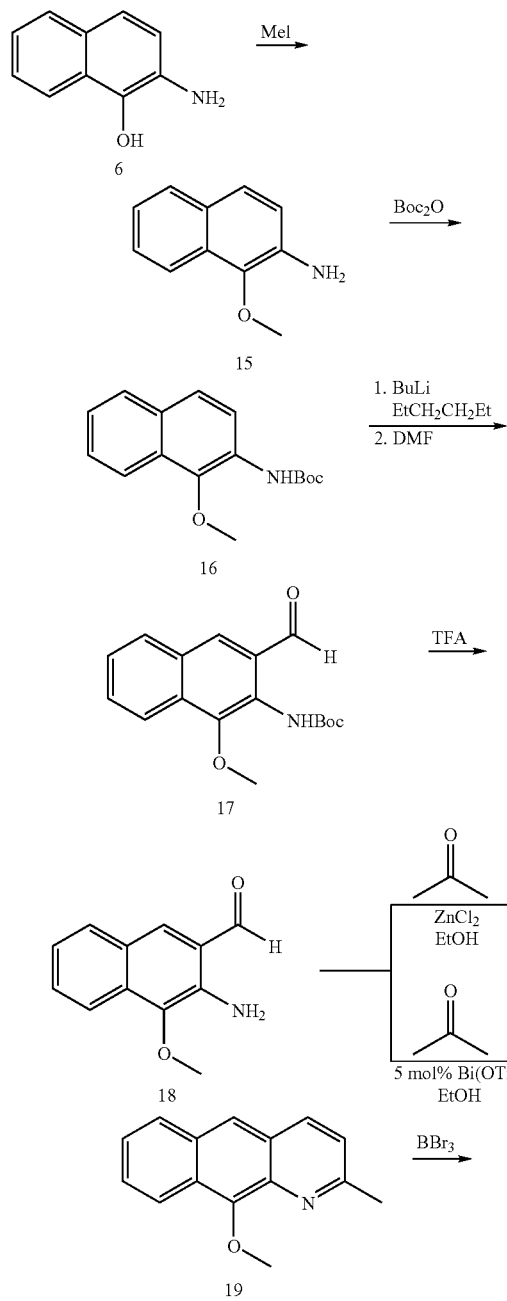

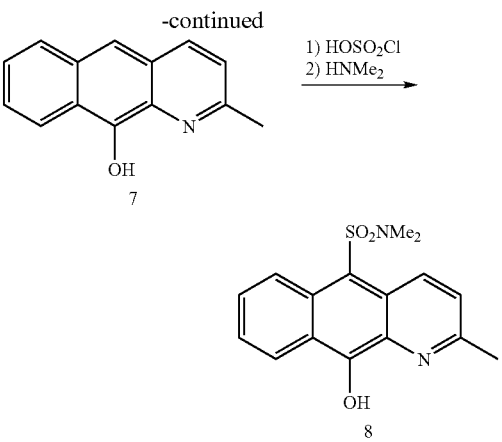

Once the three-ring chromophores are synthesized, protection of the extended 8-hydroxyquinoline (8) as the tert-butyldiphenylsilyl ether is followed by a three-step procedure to afford the bromomethyl derivative (21). Asymmetric alkylation of 21 with tert-butyl ester 22 gives the respective Sox-modified amino acid 23, which can then be converted to the Fmoc derivative 24.

Scheme 4.
General synthetic route to CHEF fluorophore.

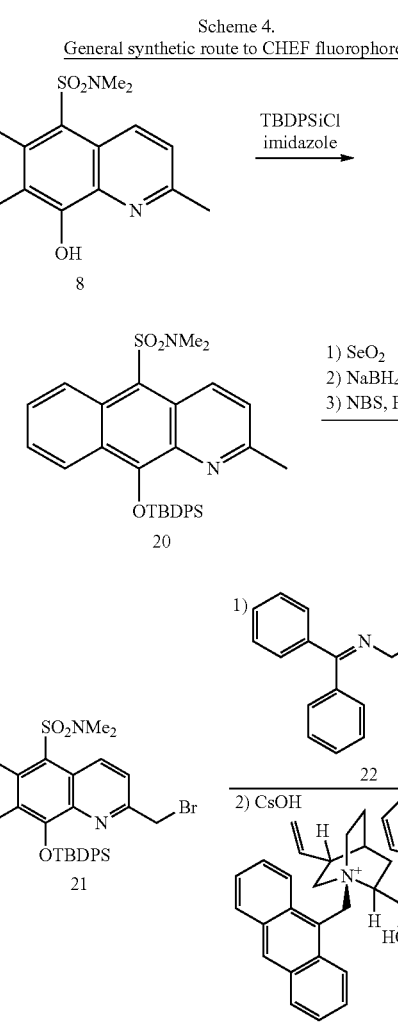

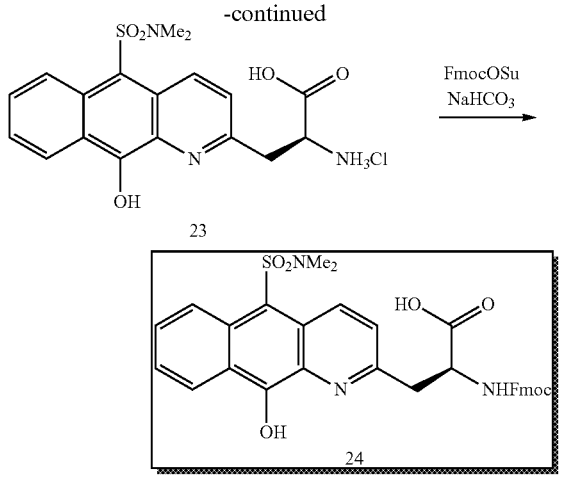

Synthesis of the Peptides:

The sensor peptides are synthesized via standard solid-phase peptide synthesis (SPPS) based on the optimal PKC$_\alpha$ peptide substrate selected from the literature (RRRKGS*FRRKA, $K_M$=3.8 μM). The peptides are synthesized containing a Cys residue with an orthogonal protecting group that is preferentially removed on resin allowing for alkylation of the sulfhydryl side chain with Sox-Br (Scheme 5).

Scheme 5.
Reagents and conditions: a. 1% TFA in CH$_2$Cl$_2$, 25° C., 1 min (10 x); b. Sox-Br, TMG, DMF, 25° C., 10 hr; c. TFA:H$_2$O:EDT:TIS (95:2.5:2.5:1%), 25° C., 2

Alternatively, a building block can be synthesized and the Fmoc-protected SOX-modified cysteine residue (Fmoc-Cys(Sox)-OH) is introduced to a peptide using standard peptide synthesis techniques.

Scheme 6.
Fmoc-Cys(Sox)-OH building block.

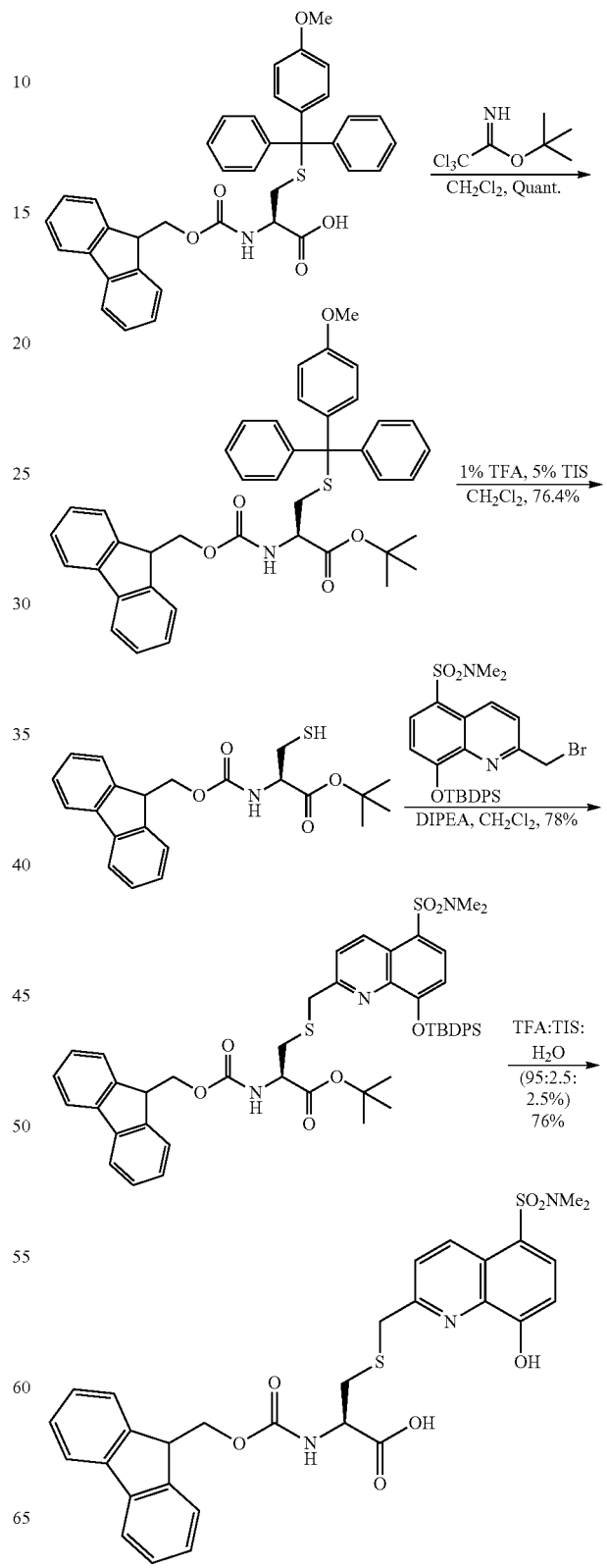

Characterization of Peptides:

Upon completion of the synthesis, peptides were cleaved and globally deprotected according to standard procedures for Fmoc-based peptide synthesis (referenced earlier), were subjected to HPLC purification and their mass was confirmed using either the ESI (Electrospray Ionization) or MALDI-TOF (Matrix Assisted Laser Desorption Ionization Time-of-Flight) mass spectrometers (Table III). (a) For all peptides except for PKCα-S10 and P10 a reverse-phase preparatory C18 column was used with the flow rate of 15 ml/min. Solvent A: $H_2O$ with 0.1% v/v TFA; solvent B: $CH_3CN$ with 0.1% v/v TFA. The run was started at 5% B (over 5 min.) and increased linearly to 50% B (over 30 min), followed by an increase to 95% B (over 1 min.) and was kept at 95% B (5 min.). For PKCα-S10 and P10, the run was started at 5% B (5 min.), increased to 15% B (1 min), followed by a linear increase to 30% B (30 min.). (b) For all peptides except for PKCα-S10 and P10 a reverse-phase analytical C18 column was used with the flow rate of 1 ml/min. Solvent A: $H_2O$ with 0.1% v/v TFA; Solvent B $CH_3CN$ with 0.1% v/v TFA. The run was started at 5% B (over 5 min.) and increased linearly to 95% B (over 30 min) and was kept at 95% B (5 min.). For PKCα-S10 and P10, the run was started at 5% B (5 min.), increased to 15% B (1 min), followed by a linear increase to 30% B (30 min.). (c) ESI-MS data was collected on a PE Biosystems Mariner mass spectrometer for all peptides.

TABLE III

HPLC, MS Characterization Data for PKC Peptides.

| Name | Peptide Sequence | Mol. Formula | Prep. HPLC Ret. Time (min)$^a$ | Anal. HPLC Ret. Time (min)$^b$ | $[M + xH]^{x+}$ Calc. | $[M + H]^+$ found$^c$ |
|---|---|---|---|---|---|---|
| PKC$_\alpha$-S10 | Ac-RRR-C(Sox)-ASFRRKA-CONH$_2$ | $C_{71}H_{118}N_{30}O_{16}S_2$ | 21.3 | 25.8 | 428.7(+4) | 429.3 |
| PKC$_\alpha$-P10 | Ac-RRR-C(Sox)-ApSFRRKA-CONH$_2$ | $C_{71}H_{119}N_{30}O_{19}PS_2$ | 23.7 | 22.9 | 448.7(+4) | 449.4 |
| PKC$_{\beta I}$-S1 | Ac-LKR-C(Sox)-ASFKKFA-CONH$_2$ | $C_{74}H_{114}N_{20}O_{16}S_2$ | 26.1 | 24.9 | 535.4(+3) | 535.3 |
| PKC$_{\beta I}$-P1 | Ac-LKR-C(Sox)-ApSFKKFA-CONH$_2$ | $C_{74}H_{115}N_{20}O_{19}PS_2$ | — | 23.4 | 562.0(+3) | 561.9 |
| PKC$_\delta$-S1 | Ac-RKRKGSF-C(Sox)-YGG-CONH$_2$ | $C_{68}H_{102}N_{22}O_{17}S_2$ | 24.1 | 23.3 | 521.9(+3) | 521.9 |
| PKC$_\delta$-P1 | Ac-RKRKGpSF-C(Sox)-YGG-CONH$_2$ | $C_{68}H_{103}N_{22}O_{20}PS_2$ | 23.3 | 22.1 | 548.6(+3) | 548.6 |

Stock Solutions:

Due to the affinity of the phosphorylated peptides for $Zn^{2+}$, the reagents with the highest purity and lowest metal content were used to avoid the necessity of removing metal ion impurities after preparations.

All stock solutions were prepared prior to the day of the assay and stored at room temperature unless otherwise indicated.

Fluorescence Experiments:

Fluorescence experiments were performed on a Fluoromax 3 from Jobin Yvon. 5 nm emission and excitation slit widths were used. For all experiments, an excitation wavelength of 360 nm was used. Enzyme assays were performed by monitoring emission at 485 nm.

Figure 2:
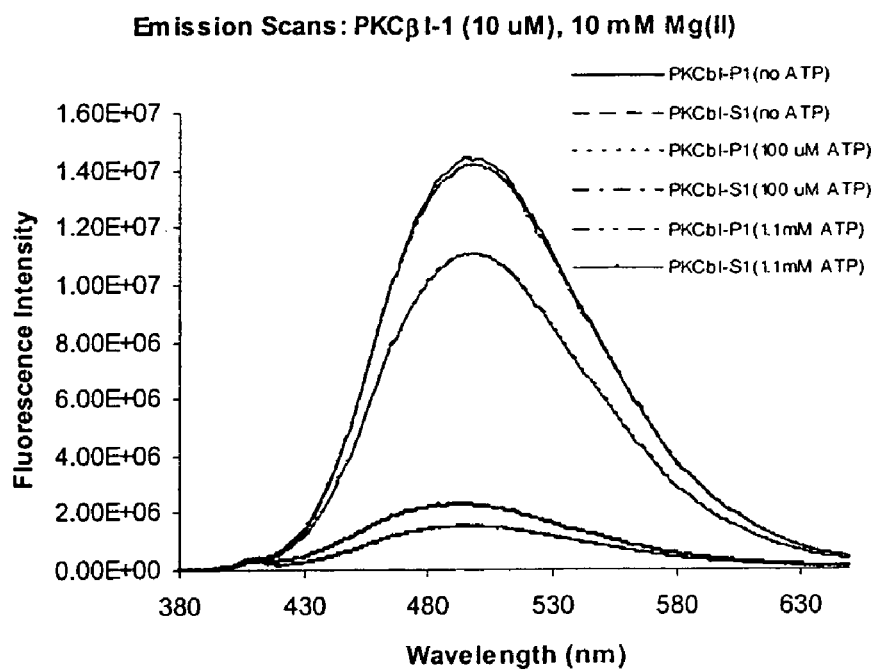
FIG. 2 is a plot of the reaction slope vs. PKC isozymes with 1 μM substrate.
Figure 2:
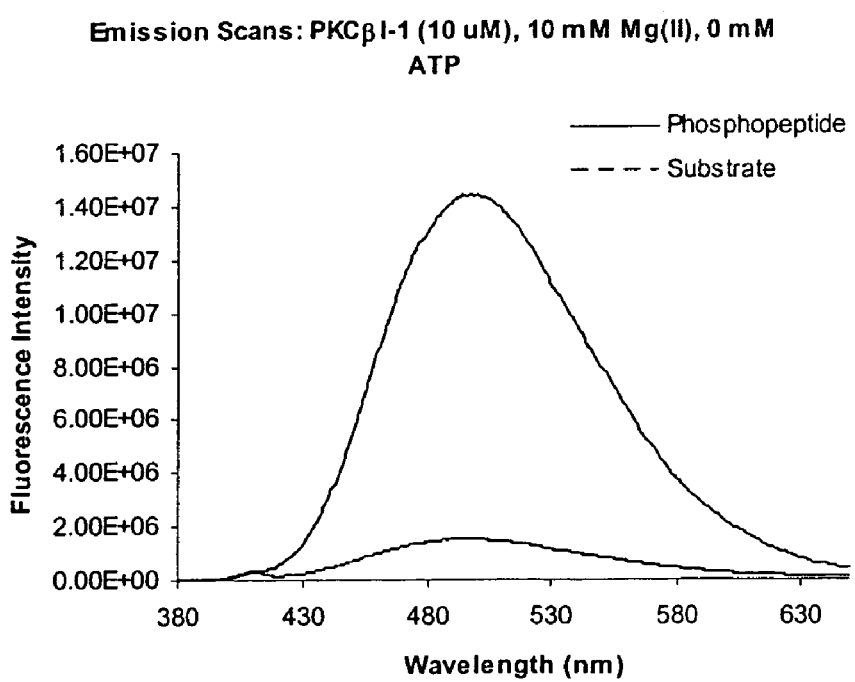
Figure 2:
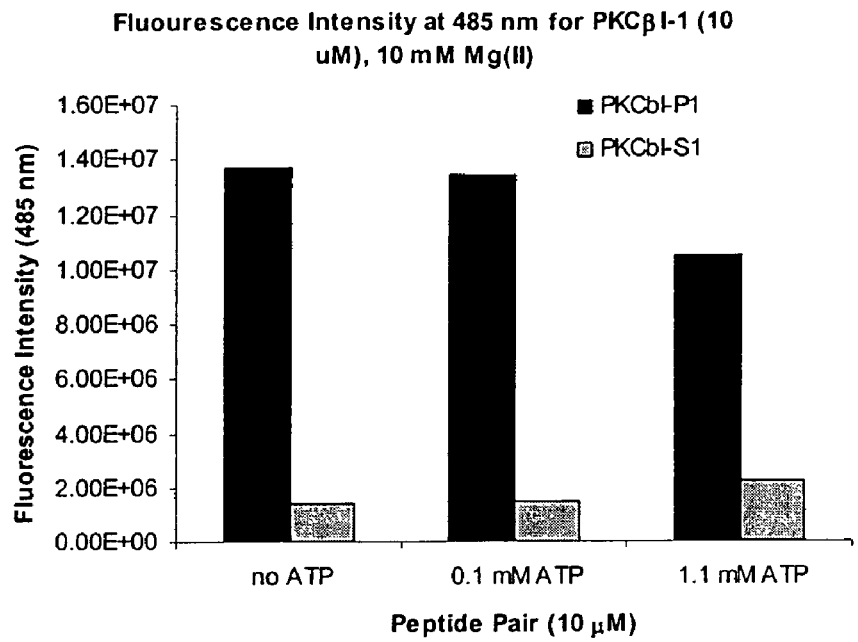
Figure 2:
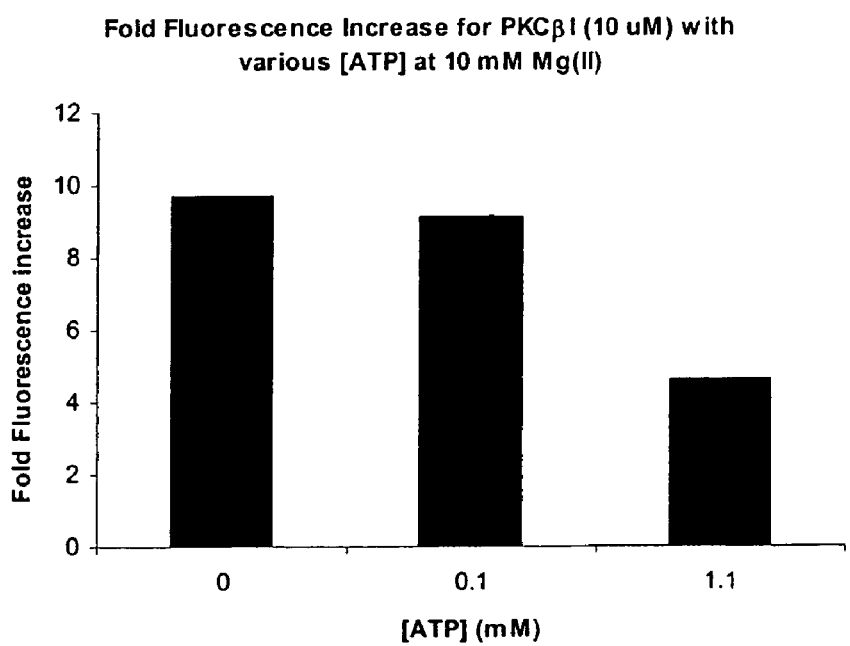

Spectral Comparison of Phosphorylated and Unphosphorylated Peptides:

After peptide characterization, emission spectra were obtained for unphosphorylated and phosphorylated peptides under appropriate conditions. The spectra were generally acquired in the presence of 10 mM $Mg^{2+}$ (although lower $Mg^{2+}$ concentrations can and have been used as well) and either 0, 0.1 or 1 mM ATP in a preselected buffer (usually 20 mM HEPES, pH 7.4). Relying on the emission spectra the fold fluorescence differences were measured by dividing the fluorescence intensity of the phosphopeptide by the fluorescence intensity of its unphosphorylated counterpart at 485 nm. FIG. 2 depicts the fluorescence spectra of the phosphorylated and unphosphorylated peptides in the appropriate assay mixture: (A) emissions scans of PKC$_{\beta I}$-1 (10 μM), 10 mM Mg(II), 3×; (B) emissions scans of PKC$_{\beta I}$-1 (10 μM), 10 mM Mg(II), 0 mM ATP, 3×; (C) fluorescence difference for PKC$_{\beta I}$-1 (10 μM), 10 mM Mg(II), 3×.

Biophysical and Kinetic Properties of the Sensors:

While the biophysical properties of a "linear" sensor for PKC$_\alpha$, PKC$_\alpha$-S1, are good (Table IV), once used in cell lysates PKC$_\alpha$-S1 is reactive toward many of the PKC isozymes present in cells. In comparison, the chemosensors with the extended recognition domain as disclosed in the present invention for PKC$_\alpha$, PKC$_{\alpha-S}$9 and PKC$_\alpha$-S10, also have good biophysical properties (Table IV). Moreover, these sensors are much more selective for PKC$_\alpha$ as is determined by obtaining kinetic parameters (Table V), and thus will be able to offer more specificity in cellular assays.

TABLE IV

Sequences, $K_D$ values and fluorescence increases of PKC peptides.

| Peptides | -5 -4 -3 | -2 | -1 0 1 2 3 4 5 | $K_D$ (mM) | Fluorescence Increase |
|---|---|---|---|---|---|
| $PKC_\alpha$-S1(P1) | Ac-Sox | P | G (p)S F R R R-$NH_2$ | 12 | 5.7 x |
| $PKC_\alpha$-S9(P9) | Ac-R R R | C(Sox) | G (p)S F R R K A-$NH_2$ | 47 | 3.5 x |
| $PKC_\alpha$-S10(P10) | Ac-R R R | C(Sox) | A (p)S F R R K A-$NH_2$ | 24 | 3.9 x |

TABLE V

Kinetic parameters of the peptides with $PKC_\alpha$.

| Peptides | -5 -4 -3 | -2 | -1 0 1 2 3 4 5 | $K_M$ (μM) | $V_{max}$ (μmol $min^{-1}$ $mg^{-1}$) | $V_{max}/K_M$ ($min^{-1}$ $mg^{-1}$) |
|---|---|---|---|---|---|---|
| $PKC_\alpha$-S1(P1) | Ac- Sox | P | G (p)S F R R K A-$NH_2$ | 8.6 ± 2.9 | 5.9 ± 1.9 | 6200 |
| $PKC_\alpha$-S9(P9) | Ac-R R | C(Sox) | G (p)S F R R K A-$NH_2$ | 0.093 ± 0.017 | 1.8 ± 0.12 | 160000 |
| $PKC_\alpha$-S10(P10) | Ac-R R | C(Sox) | A (p)S F R R K A-$NH_2$ | 0.12 ± 0.018 | 2.2 ± 0.25 | 149000 |

Figure 3:
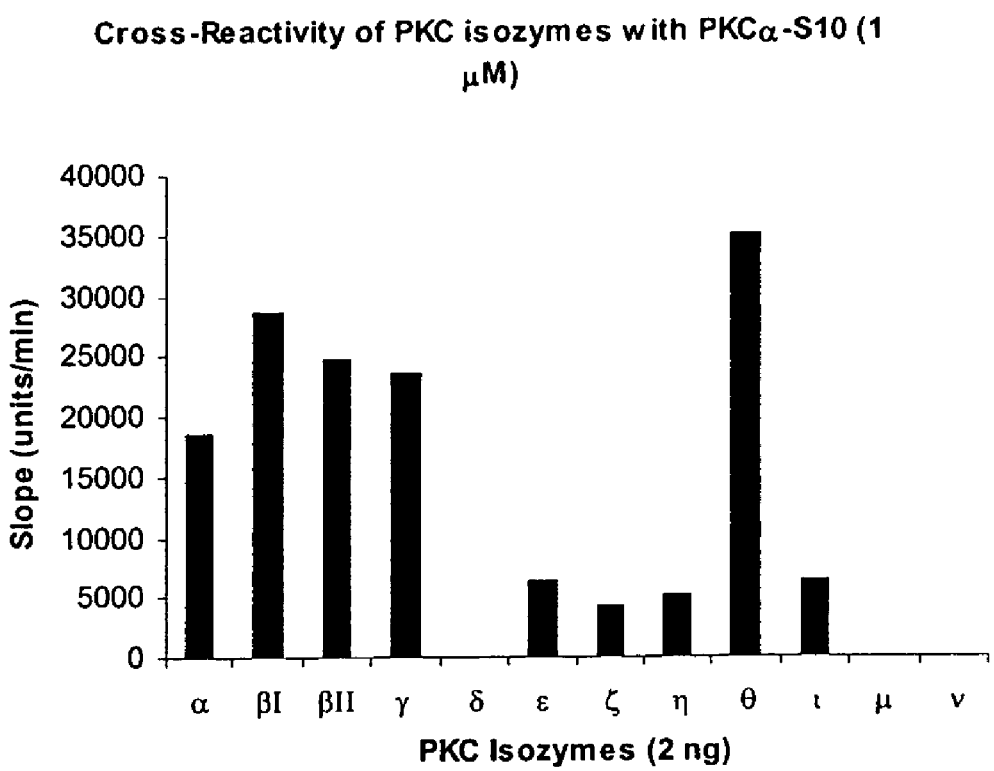
FIG. 3 shows a plot of the cross-reactivity of PKC isozymes with $PKC_\alpha$-S10.

The Cross-reactivity of the Sox Peptide:

With the kinetic parameters at hand it is possible to test the cross-reactivity of $PKC_\alpha$-S10 with PKC isozymes. In 12 separate reactions $PKC_\alpha$-S10 (1 μM) is subjected to phosphorylation with $PKC_\alpha$, $PKC_{\beta I}$, $PKC_{\beta II}$, $PKC_\gamma$, $PKC_\delta$, $PKC_\epsilon$, $PKC_\zeta$, $PKC_\eta$, $PKC_\theta$, $PKC_\iota$, $PKC_\mu$ and $PKC_\nu$ (2 ng). Under these conditions $PKC_{\beta I}$ and $PKC_\theta$ are slightly more active than $PKC_\alpha$, whereas $PKC_{\beta II}$ and $PKC_\gamma$ have comparable activities to that of $PKC_\alpha$. On the other hand, no activity is observed with $PKC_\delta$, $PKC_\mu$, and $PKC_\nu$, and very little activity is detected with $PKC_\epsilon$, $PKC_\zeta$, $PKC_\eta$ and $PKC_\iota$ (FIG. 3).

It is shown that 3 isozymes do not carry out the reaction on $PKC_\alpha$-S10 and that an additional 4 are only slightly active. Therefore, only 4 of 11 isozymes (not including $PKC_\alpha$) are able to perform phosphorylation as well or slightly better than $PKC_\alpha$. This trend has been seen previously in the literature. Cantley et al. determined $K_M$ values of a similar peptide to $PKC_\alpha$-S10 with $PKC_\alpha$, $PKC_{\beta I}$, $PKC_\delta$, $PKC_\zeta$ and $PKC_\mu$ showing that while $PKC_\alpha$ has the lowest $K_M$, the substrate is accepted almost as well by all isozymes but $PKC_\mu$. This is not surprising since these isozymes will have substrates that are very similar. This approach with the extended recognition domain as disclosed in the present invention allows for synthesis of substrates specific for certain PKC isozymes without soliciting phosphorylation from any of the other ones.

While the invention has been described with reference to certain embodiments, other features may be included without departing from the spirit and scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A compound of structure (I):

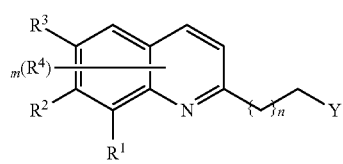

(I)

wherein $R^1$ is hydroxy, amino, or thiol;
$R^2$ and $R^3$ are each independently hydrogen, an electron-withdrawing group, or —$SO_2X$;
each $R^4$ is independently hydrogen, an electron-withdrawing group or —$SO_2X$, wherein $R^4$ can substitute any open valence of any ring within structure (I);

X is —OR' or —NR'R";

Y is halogen, —SH, —NR'R'", —CHO, or —$CO_2H$;

R' and R" are each independently hydrogen or $C_{1-6}$ alkyl;

R'" is hydrogen, unsubstituted $C_{1-6}$ alkyl, tBoc or Fmoc;

n is 0, 1, 2 or 3; and m is 1, 2, or 3, and wherein at least one of $R^2$, $R^3$ or $R^4$ is —$SO_2X$ and at least another one of $R^2$, $R^3$ or $R^4$ is an electron-withdrawing group.

2. The compound of claim 1, which has the structure:

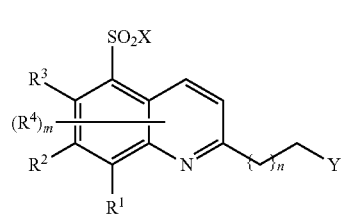

(II)

wherein $R^1$ is hydroxy, amino, or thiol;
$R^2$ and $R^3$ are each independently hydrogen, an electron-withdrawing group, or —$SO_2X$;
each $R^4$ is independently hydrogen, an electron-withdrawing group or —$SO_2X$, wherein $R^4$ can substitute any open valence of any ring within the structure;

X is —OR' or —NR'R";

Y is halogen, —SH, —NR'R'", —CHO, or —$CO_2H$;

R' and R" are each independently hydrogen or $C_{1-6}$ alkyl;

R'" is hydrogen, unsubstituted $C_{1-6}$ alkyl, tBoc or Fmoc;

n is 0, 1, 2 or 3; and m is 1 or 2, and wherein at least one of $R^2$, $R^3$ or $R^4$ is an electron-withdrawing group.

3. The compound of claim 1, which has the structure:

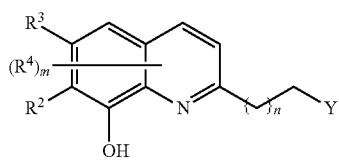

(III)

wherein $R^2$ and $R^3$ are each independently hydrogen, an electron-withdrawing group, or —$SO_2X$;
each $R^4$ is independently hydrogen, an electron-withdrawing group or —$SO_2X$, wherein $R^4$ can substitute any open valence of any ring within the structure;
X is —OR' or —NR'R";
Y is halogen, —SH, —NR'R''', —CHO, or —$CO_2H$;
R' and R" are each independently hydrogen or $C_{1-6}$ alkyl;
R''' is hydrogen, unsubstituted $C_{1-6}$ alkyl, tBoc or Fmoc;
n is 0, 1, 2 or 3; and
m is 1, 2 or 3, and
wherein at least one of $R^2$, $R^3$ or $R^4$ is —$SO_2X$ and at least another one of $R^2$, $R^3$ or $R^4$ is an electron-withdrawing group.

4. The compound of claim 1, which has the structure:

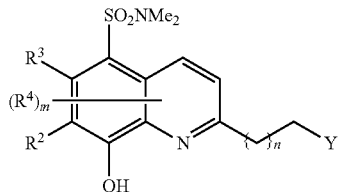

(IV)

wherein $R^2$ and $R^3$ are each independently hydrogen, an electron-withdrawing group, or —$SO_2X$;
each $R^4$ is independently hydrogen, an electron-withdrawing group or —$SO_2X$, wherein $R^4$ can substitute any open valence of any ring within the structure;
X is —OR' or —NR'R";
Y is halogen, —SH, —NR'R''', —CHO, or —$CO_2H$;
R' and R" are each independently hydrogen or $C_{1-6}$ alkyl;
R''' is hydrogen, unsubstituted $C_{1-6}$ alkyl, tBoc or Fmoc;
n is 0, 1, 2 or 3; and
m is 1 or 2, and
wherein at least one of $R^2$, $R^3$ or $R^4$ is an electron-withdrawing group.

5. A peptide comprising an amino acid residue, the side chain of the amino acid residue modified with a compound of structure (I):

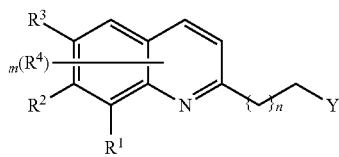

(I)

wherein $R^1$ is hydroxy, amino, or thiol;
$R^2$ and $R^3$ are each independently hydrogen, an electron-withdrawing group, or —$SO_2X$;
each $R^4$ is independently hydrogen, an electron-withdrawing group or —$SO_2X$, wherein $R^4$ can substitute any open valence of any ring within structure (I);
X is —OR' or —NR'R";
Y is halogen, —SH, —NR'R''', —CHO, or —$CO_2H$;
R' and R" are each independently hydrogen or $C_{1-6}$ alkyl;
R''' is hydrogen, $C_{1-6}$ alkyl, tBoc or Fmoc;
n is 0, 1, 2 or 3; and
m is 1, 2 or 3, 4, and
wherein at least one of $R^2$, $R^3$ or $R^4$ is —$SO_2X$ and at least another one of $R^2$, $R^3$ or $R^4$ is an electron-withdrawing group.

6. The peptide of claim 5, wherein the peptide further comprises a kinase recognition sequence.

7. The peptide of claim 5, wherein the peptide further comprises two kinase recognition sequences.

8. The compound of claim 1, which has the structure:

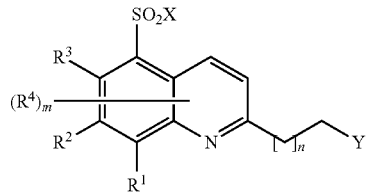

wherein $R^1$ is hydroxy, amino, or thiol;
$R^2$ and $R^3$ are each hydrogen;
each $R^4$ is independently hydrogen, an electron-withdrawing group or —$SO_2X$, wherein $R^4$ can substitute any open valence of any ring within the structure;
X is —OR' or —NR'R";
Y is halogen, —SH, —NR'R''', —CHO, or —$CO_2H$;
R' and R" are each independently hydrogen or $C_{1-6}$ alkyl;
R''' is hydrogen, unsubstituted $C_{1-6}$ alkyl, tBoc or Fmoc;
n is 0, 1, 2 or 3; and
m is 1 or 2, and
wherein at least one $R^4$ is an electron-withdrawing group.

9. The compound of claim 1, which has the structure:

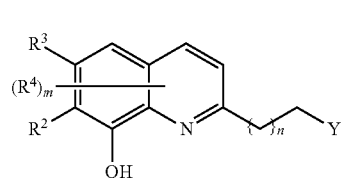

(I)

wherein $R^2$ and $R^3$ are each hydrogen;
each $R^4$ is independently hydrogen, an electron-withdrawing group or —$SO_2X$, wherein $R^4$ can substitute any open valence of any ring within the structure;
X is —OR' or —NR'R";
Y is halogen, —SH, —NR'R''', —CHO, or —$CO_2H$;
R' and R" are each independently hydrogen or $C_{1-6}$ alkyl;
R''' is hydrogen, unsubstituted $C_{1-6}$ alkyl, tBoc or Fmoc;
n is 0, 1, 2 or 3; and
m is 1, 2 or 3, and
wherein at least one $R^4$ is —$SO_2X$ and at least another one of $R^4$ is an electron-withdrawing group.

10. The compound of claim 1, which has the structure:

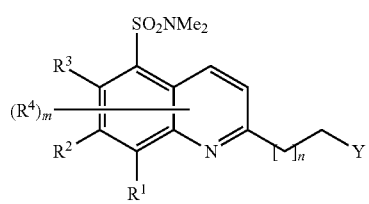

wherein $R^2$ and $R^3$ are each hydrogen;
each $R^4$ is independently hydrogen, an electron-withdrawing group or —SO$_2$X, wherein $R^4$ can substitute any open valence of any ring within the structure;
X is —OR' or —NR'R";
Y is halogen, —SH, —NR'R''', —CHO, or —CO$_2$H;
R' and R" are each independently hydrogen or C$_{1-6}$ alkyl;
R''' is hydrogen, unsubstituted C$_{1-6}$ alkyl, tBoc or Fmoc;
n is 0, 1, 2 or 3; and
m is 1 or 2, and
wherein at least one $R^4$ is an electron-withdrawing group.

* * * * *